US00PP15392P2

(12) United States Plant Patent
Bergman

(10) Patent No.: US PP15,392 P2
(45) Date of Patent: Nov. 30, 2004

(54) ***CHRYSANTHEMUM* PLANT NAMED 'YOANCHORAGE'**

(50) Latin Name: *Chrysanthemum×morifolium*
Varietal Denomination: Yoanchorage

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/437,949

(22) Filed: May 13, 2003

(51) Int. Cl.[7] ..... A01H 5/00
(52) U.S. Cl. ..... Plt./288
(58) Field of Search ..... Plt./288

*Primary Examiner*—Howard J. Locker
(74) *Attorney, Agent, or Firm*—C. A. Whealy

(57) ABSTRACT

A distinct cultivar of *Chrysanthemum* plant named 'Yoanchorage', characterized by its uniform and upright plant habit; strong and freely branching growth habit; dark green-colored foliage; uniform flowering habit; early flowering habit; large decorative-type inflorescences; white-colored ray florets; and excellent postproduction longevity with plants maintaining good substance and color for about four weeks in an interior environment.

2 Drawing Sheets

Botanical classification/cultivar designation: *Chrysanthemum×morifolium* cultivar Yoanchorage.

BACKGROUND OF THE INVENTION

The present Invention relates to a new and distinct cultivar of *Chrysanthemum* plant, botanically known as *Chrysanthemum×morifolium* and hereinafter referred to by the name 'Yoanchorage'.

The new *Chrysanthemum* is a product of a planned breeding program conducted by the Inventor in Salinas, Calif. and Fort Myers, Fla. The objective of the breeding program is to create new potted *Chrysanthemum* cultivars that are suitable for year-round production with uniform plant growth habit, good vigor, desirable inflorescence form and floret colors, fast response time, and good postproduction longevity.

The new *Chrysanthemum* originated from a cross made by the Inventor in March, 1996, in Salinas, Calif., of a proprietary *Chrysanthemum* seedling selection identified as code number YB-4620, not patented, as the female, or seed, parent with a proprietary *Chrysanthemum* seedling selection identified as code number YB-5354, not patented, as the male, or pollen, parent. The new *Chrysanthemum* was discovered and selected by the Inventor as a single flowering plant within the progeny of the stated cross grown in a controlled environment in Fort Myers, Fla. in April, 1997. The selection of this plant was based on its uniform plant growth habit, desirable inflorescence form and ray floret colors, fast response time, and excellent postproduction longevity.

Asexual reproduction of the new *Chrysanthemum* by vegetative tip cuttings was first conducted in Fort Myers, Fla. in July, 1997. Asexual reproduction by cuttings has shown that the unique features of this new *Chrysanthemum* are stable and reproduced true to type in successive generations.

SUMMARY OF THE INVENTION

The cultivar Yoanchorage has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yoanchorage'. These characteristics in combination distinguish 'Yoanchorage' as a new and distinct *Chrysanthemum*:

1. Uniform and upright plant habit.
2. Strong and freely branching growth habit.
3. Dark green-colored foliage.
4. Uniform flowering habit.
5. Early flowering, 8-week response time.
6. Large decorative-type inflorescences.
7. White-colored ray florets.
8. Excellent postproduction longevity with plants maintaining good substance and color for about four weeks in an interior environment.

Plants of the new *Chrysanthemum* differ primarily from plants of the female parent selection in ray floret coloration as plants of the new *Chrysanthemum* have white-colored ray florets whereas plants of the female parent selection have golden bronze-colored ray florets. In addition, plants of the new *Chrysanthemum* are more vigorous than plants of the female parent selection.

Plants of the new *Chrysanthemum* differ primarily from plants of the male parent selection in ray floret shape as plants of the new *Chrysanthemum* have elongated oblong-shaped ray florets whereas plants of the male parent selection have spoon-shaped ray florets. In addition, plants of the new *Chrysanthemum* have smaller inflorescences with fewer disc florets than plants of the male parent selection.

Plants of the new *Chrysanthemum* can be compared to plants of the cultivar Surf, disclosed in U.S. Plant Pat. No. 4,585. In side-by-side comparisons conducted in Salinas, Calif., plants of the new *Chrysanthemum* differed from plants of the cultivar Surf in the following characteristics:

1. Plants of the new *Chrysanthemum* were more upright than and not as outwardly spreading as plants of the cultivar Surf.

2. Plants of the new *Chrysanthemum* had larger inflorescences than plants of the cultivar Surf.
3. Plants of the new *Chrysanthemum* were more tolerant to high production temperatures than plants of the cultivar Surf.

BRIEF DESCRIPTION OF THE PHOTOGRAPHS

The accompanying colored photographs illustrate the overall appearance of the new *Chrysanthemum* showing the colors as true as it is reasonably possible to obtain in colored reproductions of this type. Colors in the photographs may differ from the color values cited in the detailed botanical description which accurately describe the colors of the new *Chrysanthemum.*

The photograph on the first sheet comprises a side perspective view of typical flowering plants of 'Yoanchorage' grown as disbud-types.

The photograph on the second sheet comprises a close-up view of typical inflorescences of 'Yoanchorage' grown as disbud-types.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the fall in Salinas, Calif., in a fiberglass-covered greenhouse and under conditions which approximate those generally used in commercial potted *Chrysanthemum* production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about 14 days later. At the time of the pinch, the photoinductive short day/long night treatments were initiated. Plants used for the photographs and description were grown as disbud-types. Measurements and numerical values represent averages of typical flowering plants.

Botanical classification: *Chrysanthemum×morifolium* cultivar Yoanchorage.

Commercial classification: Decorative-type potted *Chrysanthemum.*

Parentage:

*Female, or seed, parent.*—Proprietary *Chrysanthemum×morifolium* seedling selection identified as code number YB-4620, not patented.

*Male, or pollen, parent.*—Proprietary *Chrysanthemum×morifolium* seedling selection identified as code number YB-5354, not patented.

Propagation:

*Type.*—Terminal tip cuttings.

*Time to initiate roots.*—About four days at 21° C.

*Time to produce a rooted cutting.*—About ten days at 21° C.

*Root description.*—White, close to 155D; fibrous.

*Rooting habit.*—Freely branching.

Plant description:

*Appearance.*—Herbaceous decorative-type potted *Chrysanthemum* that is typically grown as a disbud-type, but can be grown as a spray-type. Uniform with lateral branches mostly upright; uniformly flat crown. Strong and freely branching growth habit; about four to five lateral branches develop after removal of terminal apex (pinching); dense and full plants.

*Plant height.*—About 29 cm.

*Plant width.*—About 35 cm.

*Lateral branches* (*peduncles*).—Length: About 22.5 cm. Diameter: About 4.5 mm. Internode length: About 1.1 cm. Strength: Strong. Texture: Pubescent. Color: Close to 146A.

*Foliage description.*—Arrangement: Alternate; simple. Length: About 6.8 cm. Width: About 5.4 cm. Apex: Mucronate. Base: Attenuate with truncate tendencies. Margin: Palmately lobed, sinuses between lateral lobes mostly parallel. Texture, upper surface: Sparsely pubescent. Texture, lower surface: Pubescent; veins prominent. Color: Developing and fully expanded foliage, upper surface: 147A. Developing and fully expanded foliage, lower surface: 147B. Venation, upper and lower surfaces: 147A to 147B. Petiole length: About 2.6 cm. Petiole diameter: About 3 mm. Petiole color, upper and lower surfaces: 146A.

Inflorescence description:

*Appearance.*—Decorative-type inflorescence form with elongated oblong-shaped ray florets. Inflorescences borne on terminals above foliage. Disk and ray florets develop acropetally on a capitulum. Inflorescences not fragrant. Plants are typically grown as disbud-types, but can be grown as spray-types.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering plants exposed to two weeks of long day/short night conditions followed by photoinductive short day/long night conditions flower about eight weeks later.

*Postproduction longevity.*—Inflorescences maintain good color and substance for about four weeks in an interior environment.

*Quantity of inflorescences.*—Grown as a disbud-type, only one inflorescence, the terminal inflorescence, develops per lateral branch.

*Inflorescence bud.*—Height: About 8 mm. Diameter: About 1 cm. Shape: Oblate. Color: Close to 146A to 147A.

*Inflorescence diameter.*—About 10.75 cm.

*Inflorescence depth* (*height*).—About 3.6 cm.

*Diameter of disc.*—About 5 mm; inconspicious.

*Receptacle diameter.*—About 8 mm.

*Ray florets.*—Shape: Elongated oblong. Orientation: Initially upright, then perpendicular to the peduncle. Aspect: Initially incurved, eventually reflexing. Length: About 5.6 cm. Corolla tube length: About 1.2 mm. Width: About 1.4 cm. Apex: Acute to emarginate. Base: Fused into a corolla tube. Margin: Entire. Texture: Smooth, glabrous, satiny. Number of ray florets per inflorescence: About 247 arranged in numerous whorls. Color: When opening and fully opened, upper surface: Close to 155D. When opening and fully opened, lower surface: Close to 155D.

*Disc florets.*—Arrangement: Massed at center of receptacle. Shape: Tubular, elongated. Apex: Five-pointed. Length: About 6 mm. Diameter, apex:

About 2 mm. Diameter, base: About 1 mm. Number of disc florets per inflorescence: Less than 25. Color: Immature: Close to 144A. Mature: Apex: Close to 9A. Mid-section: Close to 150A. Base: Close to 155D.

*Phyllaries.*—Quantity per inflorescence: About 22. Length: About 1 cm. Width: About 4 mm. Shape: Deltoid. Apex: Acute. Base: Truncate. Margin: Entire. Texture, upper surface: Waxy, smooth. Texture, lower surface: Pubescent. Color, upper surface: Close to 146A. Color, lower surface: Close to 146A to 147A.

*Reproductive organs.*—Androecium: Present on disc florets only. Anther color: Close to 12A. Pollen amount: None observed. Gynoecium: Present on both ray and disc florets. Style color: Close to 144B to 144C. Stigma color: Close to 9A.

*Seed/fruit.*—Seed and fruit production has not been observed.

Disease/pest resistance: Resistance to pathogens and pests common to *Chrysanthemums* has not been observed on plants grown under commercial greenhouse conditions.

It is claimed:

1. A new and distinct cultivar of *Chrysanthemum* plant named 'Yoanchorage', as illustrated and described.

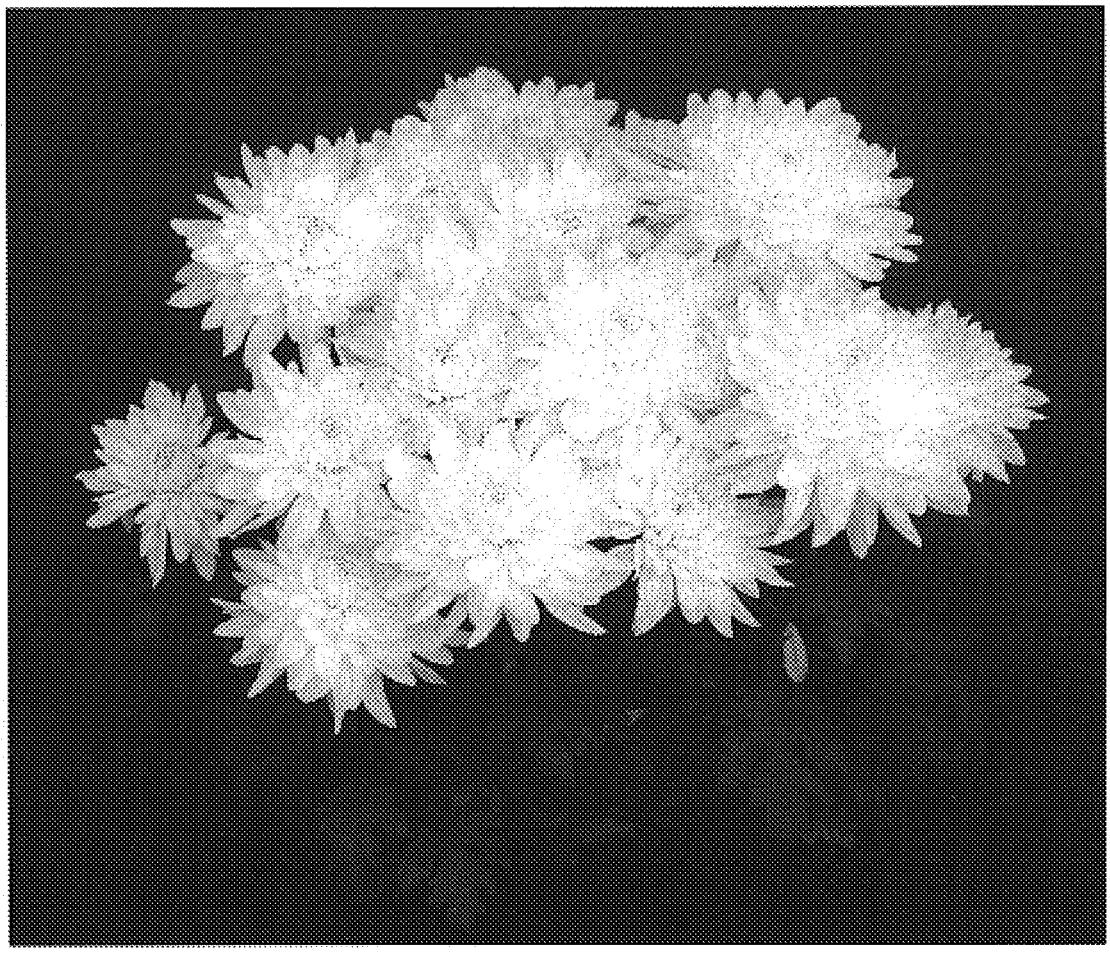

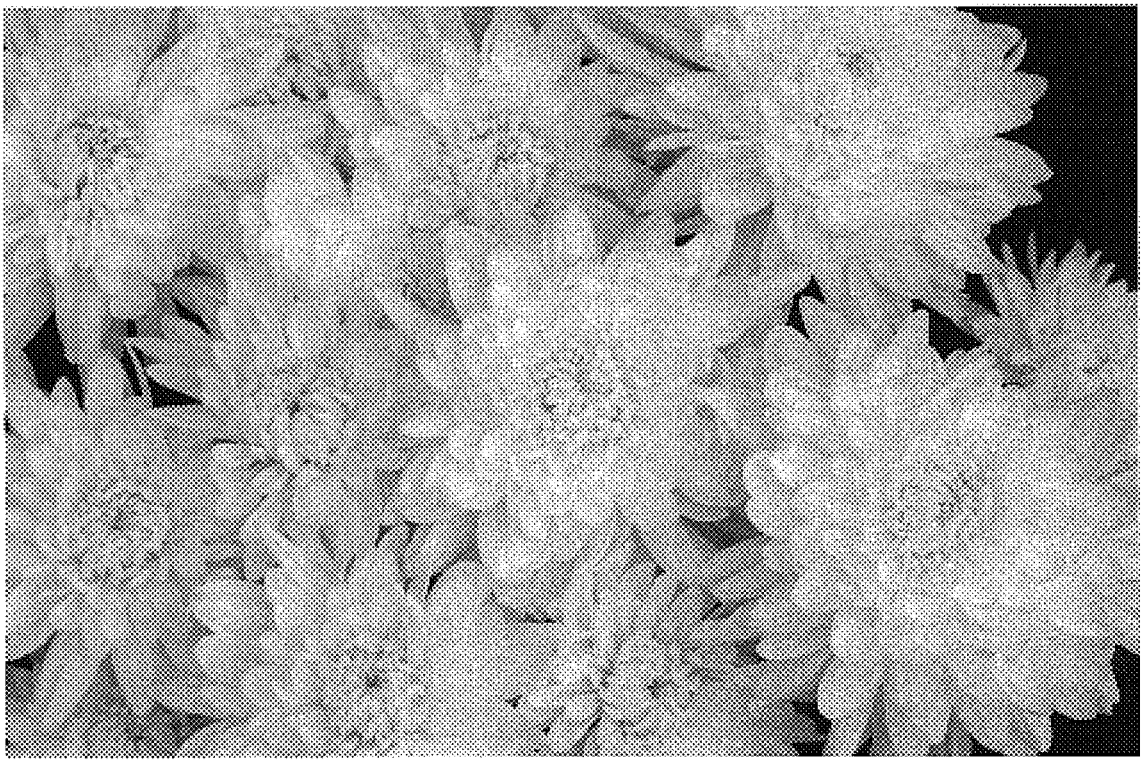

* * * * *